United States Patent [19]

Pflibsen et al.

[11] Patent Number: 4,991,953

[45] Date of Patent: Feb. 12, 1991

[54] SCANNING LASER VITREOUS CAMERA

[75] Inventors: Kent P. Pflibsen, Tuscon, Ariz.; Yakov Reznichenko, Brookline, Mass.

[73] Assignee: Eye Research Institute of Retina Foundation, Boston, Mass.

[21] Appl. No.: 308,898

[22] Filed: Feb. 9, 1989

[51] Int. Cl.$^5$ ........................... A61B 3/14; A61B 3/10
[52] U.S. Cl. ................................... 351/206; 351/205; 351/214; 351/221
[58] Field of Search ............... 351/205, 206, 221, 214, 351/207, 208; 354/62

[56] References Cited

U.S. PATENT DOCUMENTS 4,170,398 10/1979 Koester ............................... 350/6.8
4,838,679 6/1989 Bille ................................. 351/221 X

FOREIGN PATENT DOCUMENTS 61-5730 10/1977 Japan .

OTHER PUBLICATIONS

Koester, C. J. *Scanning Mirror Microscope with Optical Sectioning Characteristics: Applications in Ophthamology*, Applied Optics vol. 19, No. 11, pp. 1749–1757, 6/80.
Rioux, Marc et al. *Design of a Largedepth of View Three-Dimensional Camera for Robot Vision*, Optical Engineering, vol. 26, No. 12, pp. 1245–1250.
Bickel, G. et al., *Triangulation with Expanded Range of Depth*, Optical Engineering, vol. 24, No. 6, pp. 975–977, 12/85.

*Primary Examiner*—Rodney B. Bovernick
*Attorney, Agent, or Firm*—Lahive & Cockfield

[57] ABSTRACT

An instrument for imaging the vitreous of an eye wherein first and second windows in the iris plane accommodate a slit illumination or observation beam, and the two beams are synchronously scanned. Both beams pass through a common objective optical system, including an aspheric ophthalmic lens, and the observation beam is descanned by a mirror and spatially filtered by an observation slit conjugate to the slit which forms the illumination beam. Lateral position or width adjustment of a slit varies the axial extent or position of the focal region, to produce an image free of retinal reflection. Slit width may be increased to simultaneously image with good resolution and contrast all planes within a broad range of depths. In one binocular embodiment, the observation and illumination paths are alternately interchanged to produce a pair of stereo images formed along identical, but reversed, optical paths with a single set of optics. In a different embodiment, a common scanning element illuminates the vitreous, which is viewed along symmetrical left and right observation imaging paths. Different means of synchronous scanning and of forming a binocular image are shown. A descanned time varying line image may be converted to an electrical image signal, or may be optically rescanned to expose a photographic plate or form a directly viewable image.

30 Claims, 7 Drawing Sheets

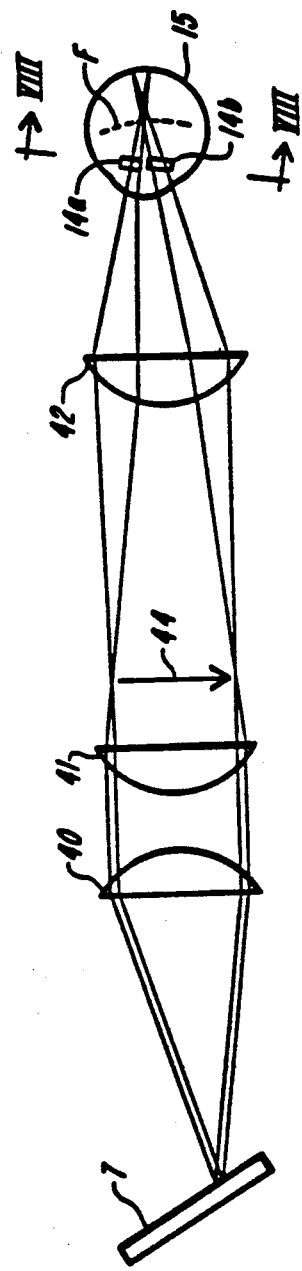
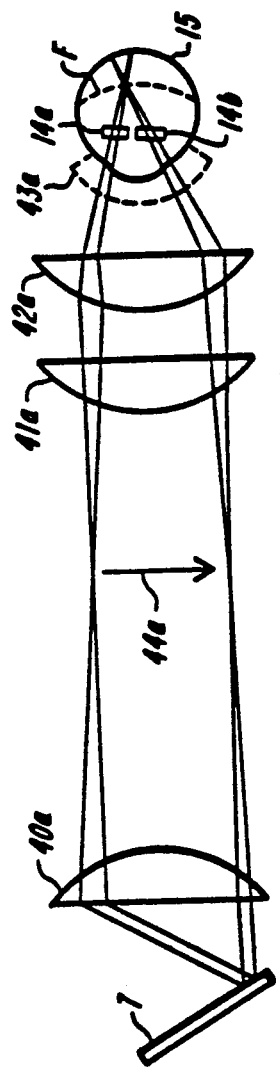
FIG. 4
FIG. 4A

SCANNING LASER VITREOUS CAMERA

BACKGROUND

The present invention relates to the field of ophthalmic microscopy and photography, and more particularly to instruments for imaging structures located in the interior of the eye. Such imaging poses a number of technical problems. The eye is filled with vitreous humor, a fluid which may have differing clarity or scattering properties, depending on the patient's health and the illumination wavelengths employed, and all illumination or observation of interior structures relies on one or more optical paths passing through a small region, i.e., the iris. These factors limit the quality of attainable images, and in particular limit the attainment of high contrast. Other complicating factors include aberrations introduced by the curved eye geometry, and interfering reflections from eye tissue, particularly from the retina. Such factors affect both the quality of the image and the area over which acceptable imaging can be performed.

For imaging the fundus, many of these problems have been addressed by recently-developed scanning laser microscopes which illuminate a small area at any given instant, thus allowing very precise control of the illuminating and observation paths, and permitting reduction of scattered light by different combinations of path separation or spatial or temporal filtering of the collected light to enhance a scanned image.

In addition, various special techniques are used for observing different particular tissues in the eye. However, observation of the vitreous humor has remained problematic, for all of the reasons noted above, and further because the humor itself is a shifting fluid of low inherent visibility or reflectance compared to the background scattering and reflectances.

SUMMARY OF THE INVENTION

Accordingly, it is an object of the invention to provide an instrument for imaging the vitreous humor of an eye.

It is another object to provide a binocular imaging instrument for imaging the vitreous humor.

It is another object to provide a stereo viewing or imaging instrument for performing measurements in the vitreous.

It is another or further object to provide an ophthalmic imaging instrument having improved depth of field and improved coverage.

These and other features of the invention are achieved by an imaging instrument wherein optics define first and second symmetrically-placed windows in the iris through which a slit illumination and an observation beam synchronously scan a region of the vitreous.

Both beams pass through a common objective lens system including an aspheric ophthalmic lens, and the observation beam is descanned by a mirror and spatially filtered through an observation slit in a plane conjugate to the slit which forms the illumination beam. The observation and imaging beams may be focused at any depth in the vitreous, and sweep out a broad imaging field free of retinal reflection. The width of a slit may be broadened to increase the axial extent of the imaged field, so as to simultaneously image with good resolution and contrast all planes within a broad range of depths. The slit width is narrowed to achieve fine axial resolution.

In a preferred embodiment, the observation and illumination paths are alternately interchanged to produce a pair of stereo images formed along identical optical paths. In a different embodiment, a common scanning element illuminates the vitreous, which is viewed along symmetrical left and right observation imaging paths. Different means of synchronous scanning with a single set of objective optics, and different means of forming a binocular image are shown. The observation light is descanned to form a time varying line image, which may be converted to an electrical image signal, or may be optically rescanned to expose a photographic plate or form a directly viewable image.

BRIEF DESCRIPTION OF DRAWINGS

These and other advantageous features of the invention will be understood from the following description, together with the drawings, wherein:

FIG. 4 shows one construction of an objective assembly;

FIG. 4A shows a preferred construction of an objective assembly;

DESCRIPTION

According to a basic aspect of the invention, a scanning element scans an image of a first illuminated slit across a portion of an ophthalmic lens, which sweeps the resulting slit illumination across a focal region in the vitreous humor of an eye, and the same lens and a second scanning element receive and descan the illuminated portion of the region by directing observation light onto a second slit which is optically conjugate to the image of the first slit. The light passed by the second slit constitutes the image of the scanned region. In its passage from the first to the second scanning elements, the illumination and observation light passes through a pair of fixedly-spaced "windows" in the pupil of the eye which define a stereo base for all observed images.

Figure 1:
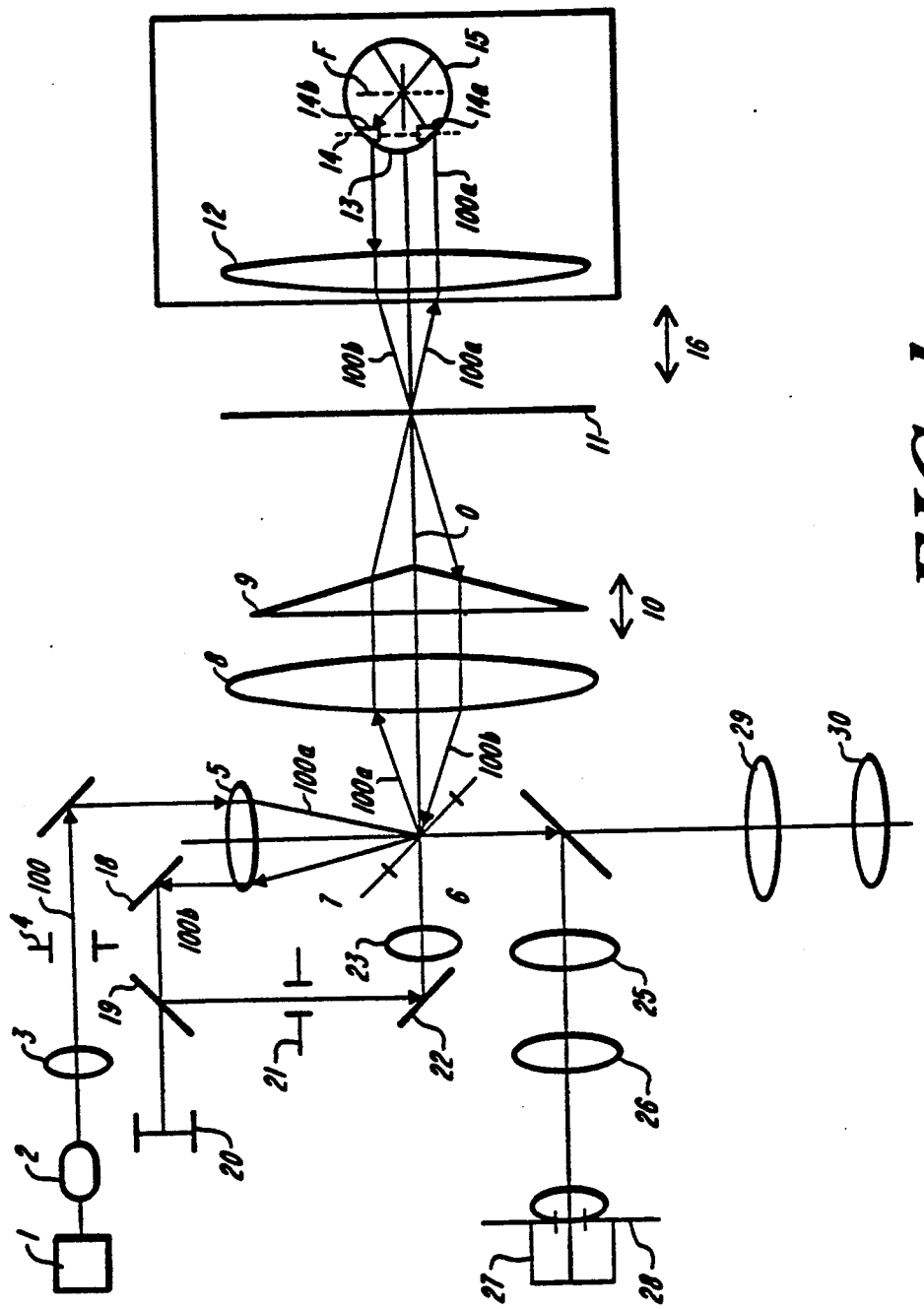
FIG. 1 is a schematic diagram of a first embodiment of an imaging and observation instrument according to the invention.

As shown in FIG. 1, a laser source 1 emits a beam of light which passes through a beam expander 2 and cylindrical lens 3, and through a slit diaphragm 4 of adjustable width placed in the focal plane of and aligned with lens 3. Slit 4 is at the front focus of a relay lens 5 which collimates the slit image and direct it at a stop 6 at the central turning axis of the face of a scanning mirror 7. The mirror turns or oscillates about the axis to scan the slit beam 100 into an objective optics system 8, 9, 12 directed at the eye 15 of a subject.

The objective optics include a first axially movable objective system 10 including an imaging lens 8 which is preferably a telecentric lens, as discussed in greater detail below, and a prism or wedge 9. Prism 9 is located just before or after the imaging lens 8, and serves to deflect the illuminating and imaging paths in first and second distinct directions, providing precise and jitter-free optical signal separation.

The prism accomplishes this by providing two faces 9a, 9b at slight angles with their apex centered at the optical axis of the objective system, such that light following the optical path through slit 4 passes through face 9a, while light directed along a slightly offset path at mirror 6 passes through face 9b. This provides two distinct optical paths through the pivoting mirror stop which pass through a common objective system. For clarity in FIG. 1, the illumination and observation paths are denoted 100a and 100b, respectively. Prism 9 and lens 8, together with a front objective lens 12 image the stop 6 as two stops or windows 14a, 14b in the pupil plane 14 of the eye. The two windows are decentered by a distance b/2 from the central axis 0 of the system, where the distance b provides a triangulation base for observations. Preferably, as discussed further below in connection with FIG. 4, the objective optics preserve the pupil separation b fixed while allowing adjustment of the focus within the vitreous and of the total image magnification.

The overall operation of the system is as follows.

The mirror 7 rotates or oscillates to scan the angular field to be viewed. The illumination beam 100a is reflected, at stop 6, at the focus of lens 8, by the mirror. The beam is then deflected by the prism 9 and passes through optics 12 to the illumination pupil 14a in the eye under observation. It thereafter comes to a narrow slit focus in a focal region F in the vitreous ahead of the retina. The eye objective 12 is preferably an aspheric lens arranged with the iris at its focal plane. The aspherism is calculated such that the scanning windows remain within the iris and maintain a constant spacing between the windows. As the mirror scans, the beam 100a sweeps across the focal region, covering a field which may constitute sixty degrees or more as it sweeps. The overall diameter of the beam narrows from approximately two hundred microns to about twenty-five microns in the focal region. The focal region F is slightly curved, but for purposes of exposition is referred to below as a focal plane.

The reflected imaging light, denoted 100b, from the tissue illuminated by beam 100a returns through observation pupil 14b and is deflected by the other angled face 9b of the prism through lens 8 back to the mirror stop 6. Thus, after the imaging light reflected from the eye passes through the refracting objective system, it is reflected by mirror 7 at a different angle of incidence than was the illumination beam 100a. Lens 5 is arranged in a telecentric configuration with stop 6 of mirror 7 at its focal plane to direct the reflected imaging light to a deflecting mirror 18, whence the imaging light either passes to a CCD detector array 20, or is deflected by a further mirror element 19 to a slit aperture 21. Mirror 19 may be a beam splitter or a swing-down mirror element.

The slit aperture 21 is placed in a position confocal to an image of slit 4 or, more precisely, to the image of the slit in region F, so that it filters out substantially all light not reflected from the focal plane of the observation beam in the eye. By reflection from mirror 7 in this manner, the observation beam is descanned, so slit aperture 21 forms a stationary line, with the light flux at a given instant representative of the brightness of a corresponding line region in the eye scanned by the observation beam at that instant.

A photo sensor array which receives an image of slit 21 may be used to directly convert the light value at each point along the slit to an electrical signal representative of brightness of the scanned region of the vitreous. In that case a train of timing scan signals from the scanning mirror may be used together with the brightness signals to encode a video image. Preferably, as discussed further below, the line image is used directly to form a two-dimensional light image.

Slit 21 is of adjustable width, and is on a stage which moves laterally. By adjusting the width of slit 21 to be wider, light from different planes within the vitreous humor of eye 15 is included in the observation beam, thus varying the depth of field to include a range of image planes. Further, by shifting the slit 21 side-to-side, the angle of collection of the observation light can be adjusted to more precisely pass only the reflected light from at, ahead of, or behind the vitreous region where the illuminating beam is focused, thus effectively including or screening out light reflected from tissue posterior or anterior to the selected plane, or adjacent to the instantaneous focal region. Varying the slit width also effects a fine focus adjustment, in which the stereo acuity of the pupils 14a, 14b better resolves axially extending features in the vitreous. Thus, slit 21 is preferably adjusted to suit the degree of image quality required.

From the confocal slit 21, the imaging light is deflected by another mirror 22 to a lens 23 which is arranged in a telecentric configuration with the rear surface of mirror 7, which is also a reflective mirror surface. The rear face of mirror 7 rescans the stationary filtered imaging light from slit aperture 21 to form a two dimensional image. Preferably, the rear surface of mirror 7 deflects the imaging light to beamsplitter 24, which separates the rescanned beam into two beams, one of which is used for viewing a two dimensional image through optics 29 and 30, and the other of which is used for the recording of the image through relay and focusing optics 25 and 26, and camera 27.

In this manner, not only are separate observation and illumination paths arranged for illumination of the vitreous humor without interference from the fundus reflections, but beam separation, scanning, illumination and observation are carried out by essentially a single set of optical elements.

In the embodiment of FIG. 1, each of the assemblies 10, 16 may be independently movable to vary the focus within the eye, the total magnification, and the triangulation base between windows 14a, 14b of the pupil. Preferably, at least lens 12 is an ophthalmic lens. In one prototype embodiment, the eye objective 12 was an aspheric plano-convex ophthalmic lens, having a diameter of 136 mm and a thickness of 29 mm, with a surface sag Z defined by the elliptical equation $$Z = cv\, y^2 / (1 + \sqrt{1 - (cc-1)(cv^2 y^2)})$$

where the curvature cv was (0.013) and the conic constant cc was (−1.55). The lens was manufactured by single point diamond turning from a polymethyl methacrylate material having an index of refraction n=1.491, and was coated to minimize reflections in the 5-6,000 angstrom observation wavelength range. Using such optics on a model eye, images of the vitreous humor in a focal region or "plane" as close as one-half millimeter to the fundus were obtained with good resolution and contrast.

Figure 2:
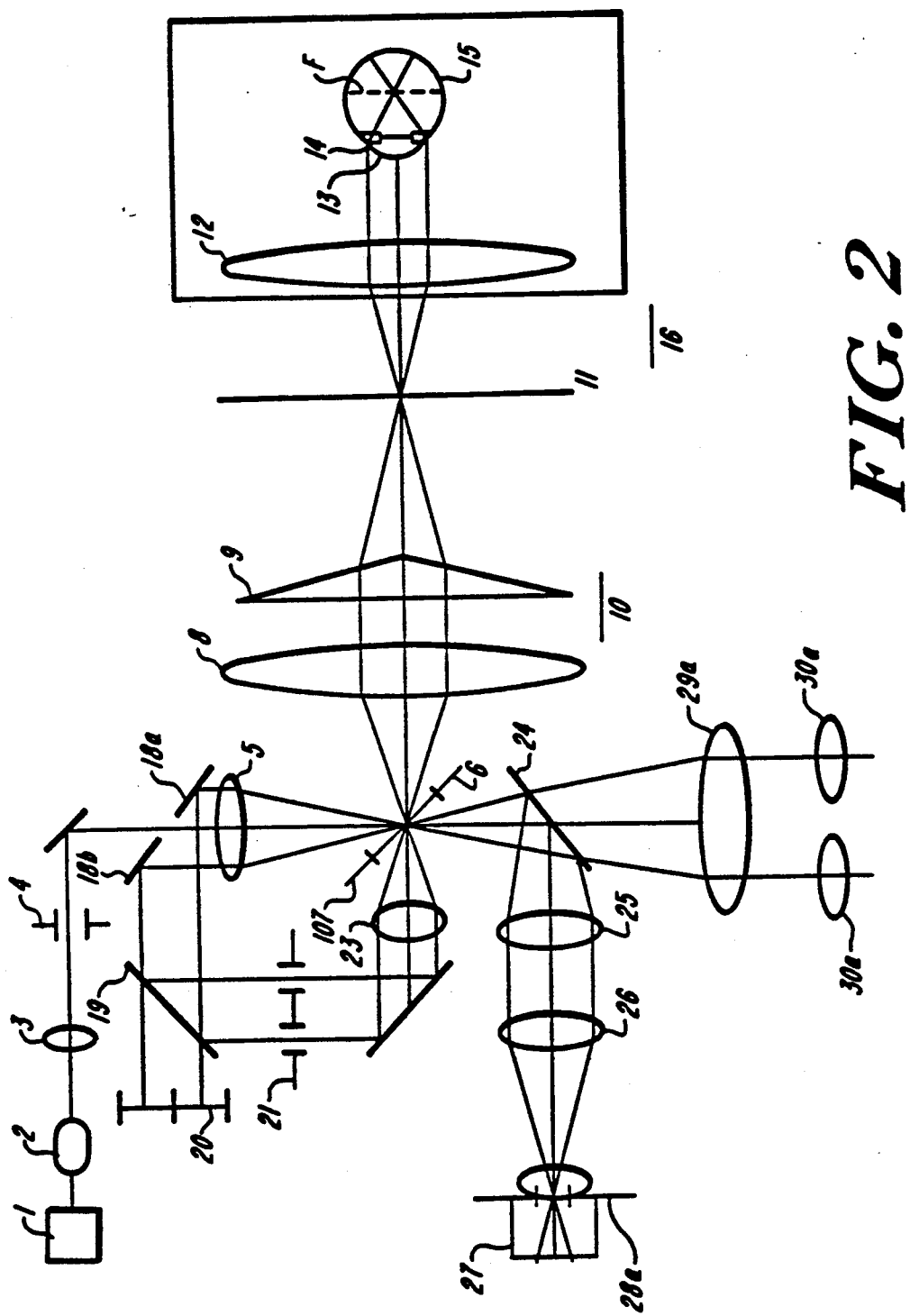
FIG. 2 shows a binocular construction based on the embodiment of FIG. 1.

FIG. 2 shows a binocular or stereo viewing embodiment of the invention based on the construction shown in FIG. 1. In this embodiment of a scanning laser vitreous camera the central scanning mirror 107, corresponding to mirror 7 of FIG. 1, is scanned over an angular range which is twice the angular range of the field to be viewed. Two distinct mirror surfaces 18a and 18b, corresponding to mirror 18 of FIG. 1, are positioned such that over one half of the scan range of mirror 107 the observation beam hits mirror 18a, while over the other half of the scan range the observation beam hits mirror 18b. Preferably 18a, 18b are adjacent portions of a single planar mirror, and the illumination beam 100a passes through a central aperture located between the portions 18a, 18b. As in the previous embodiment, the observation beams 100b directed by mirrors 18a, 18b are directed via mirror 19 to conjugate descanning slits 21, which in this case are separate, preferably adjustable, slits, which are imaged by a relay lens 23 onto a rear reflective face of mirror 107. The second mirror face thus re-scans each of the stationary slits to sweep out stereo images on a binocular eyepiece assembly 29a, 30a or stereo recording camera 28a.

In this stereo camera configuration, each of the two stereopupil images 14a, 14b located in the eye under observation is used alternately for illumination and imaging, while moving only a single mirror in the system. The same illumination beam is used for both pupils, but two different imaging beams are generated. Also, very little mechanical scan distortion is introduced into the system because the illumination and imaging pupils are located essentially at the center of rotation of the mirror 107.

The prism 9 placed after the lens 8 does not add significant distortion, but may contribute coma and astigmatism to the image. If the prism is instead placed before lens 8, some distortion is introduced, but the coma and astigmatism of the image may be dramatically reduced. A variable spacing mechanism may be provided for changing the distance between lens 8 and prism 9 to alter the separation between the illumination and imaging pupils in the eye under observation. This is useful either for changing the triangulation base to normalize a measurement or recording, or to enhance the stereo resolution of observed details by increasing the window spacing.

Other approaches to scanning and imaging a slit beam in a plane within the vitreous are also contemplated by the present invention.

Figure 3:
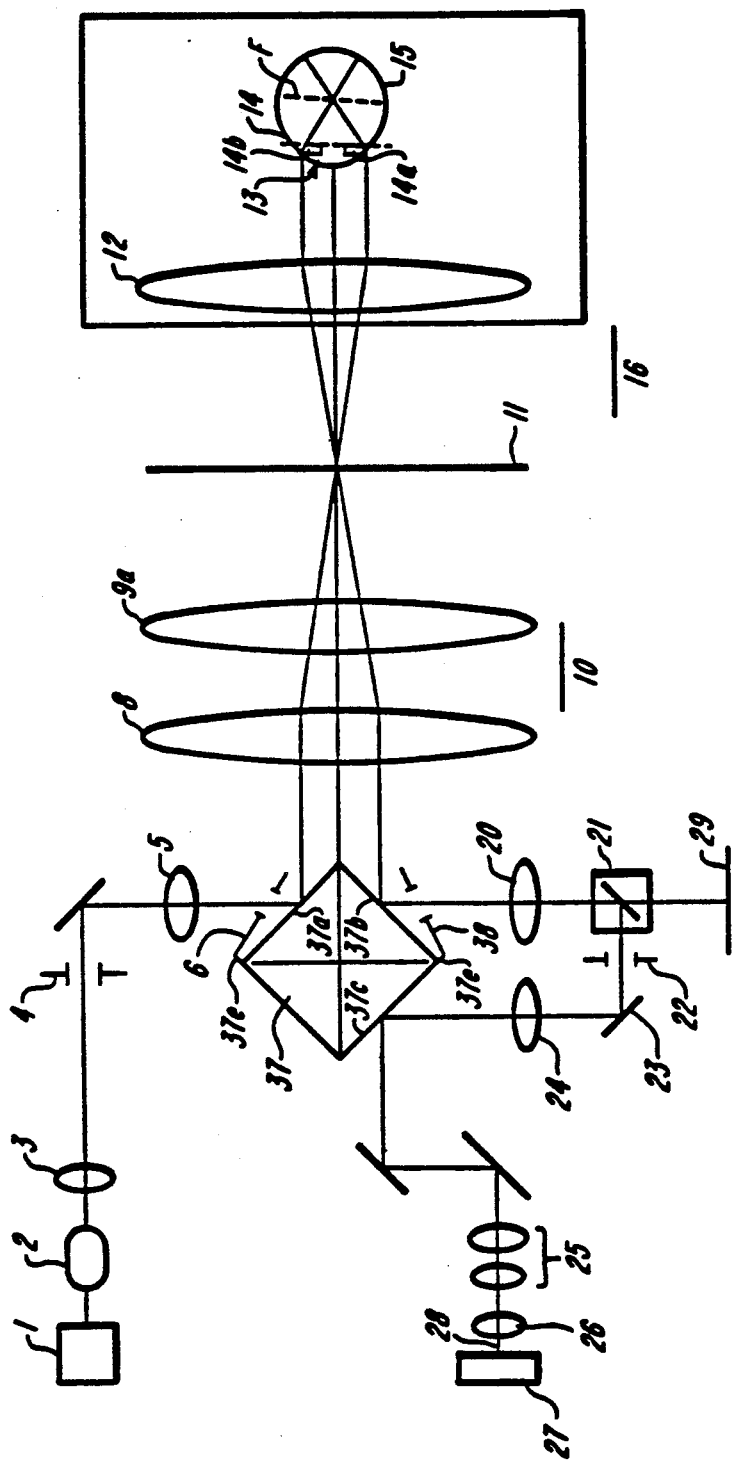
FIG. 3 shows another embodiment.

FIG. 3 shows one such different embodiment that is a monocular system wherein the bifurcation of optical paths is accomplished by reflection from two different facets of a common scanning mirror along the axis of the objective assembly. As in the embodiment of FIG. 1, a laser source 1 produces a narrow beam that passes through a beam expander 2 that increases the size of the beam to the size of the desired illumination slit. Then the beam passes through a cylindrical condenser lens 3, that forms a vertical line image in its focal plane, where a slit diaphragm 4 of adjustable width is placed. An illumination lens 5 with slit 4 at its focus creates a collimated slit beam and projects it to an artificial illumination pupil 6 placed in the focal plane of the illumination lens 5. After this the beam comes to the first face 37a of a reflective scanning prism 37, which deflects the beam in a horizontal direction and projects it to a transmission optical system.

The transmission optical system includes three major components. The first two are lenses 8 and 9a which are movable independently along the optical axis by a mechanical stage or focusing device 10, and constitute parts of a zoom system which varies the magnification of the beam. In all zoom positions the back focus of the components 8 and 9a is placed in the pupil 6 several millimeters from the face 37a of the reflecting prism 37. The slit image of the illumination slit 4 is located in the front focus of the components 8 and 9a in plane 11. The third component 12 of the transmission optical system is an ophthalmic lens which projects the slit image plane 11 to the object optical system denoted by reference numeral 13, and projects the artificial illumination pupil 6 to the pupil plane 14 of the eye. The object optical system 13 may be the bare eye, with its attendant refractive properties, or may include a contact lens as known in the art. The image of pupil 6 formed in the pupil plane 14 is decentered from the optical axis by b/2, where b is a fixed spacing which denotes the triangulation base. A second stage or focusing adjustment device 16 moves optical component 12 together with the eye 15 to vary the distance between the slit image plane 11 and optical component 12 while holding the distance between component 12 and eye 15 constant.

After reflecting from the object observation plane F within the eye, the reflected imaging light from the slit beam passes as an observation beam in the reverse direction through the optical components 12, 9a, 8 and comes to a second face 37b of the scanning prism 37. An artificial observation pupil 38 is placed several millimeters from face 37b to filter out light other than from the window 14b.

Face 37b of scanning prism 37 deflects the observation beam in the horizontal direction by the same angle as the illumination beam only with opposite sense. As the result, the light passing through artificial pupil 38, which is conjugate to observation pupil 14b and is located in the effective back focal plane of the components 8 and 9a, is descanned. The image 14b of the confocal artificial pupil 38 is located in the plane of the eye's iris 14 and is displaced by the same distance b/2 from the central axis as the image of the illumination pupil, only in the opposite direction, thus creating a triangular base b in the iris plane.

In FIG. 3, each of the artificial pupils 6, for illumination, and 38, for observation, are shown closely spaced to the respective reflecting face 37a, 37b. In order to achieve an effectively thin slit aperture while attaining a wide scan range, each artificial pupil was formed by an aperture plate secured to the mirror assembly 37 by a bracket 37e which rigidly holds the aperture plate close to the mirror face, so that the plate co-rotates with the scanning mirror. The view of FIG. 3 may be taken as a top view of this arrangement. This assures that the mirror effects a wide scan for illumination and observation without occlusion by the apertures 6, 38.

Continuing with a description of the observation optical path, the light at artificial pupil 38 is collected by a confocal lens 20 and reflected by a beam splitter 21 to a confocal slit diaphragm located at the back focal plane of lens 20 and conjugate to the imaged plane F of the eye. Slit 22 is of adjustable width, and preferably is also laterally adjustable to allow centering of the received observation beam thereon, as discussed above for the corresponding slit 21 of embodiments of FIGS. 1 and 2.

Slit 22 acts as a spatial filter. When the slit is properly aligned and its width approximates that of beam-forming slit 4, the light passing through the slit is essentially the light reflected from material in the focused illumination slit in plane F of the vitreous humor. By adjusting the slit wider, light from surrounding planes ahead of and behind the focal plane is included in the observation beam, so that it is possible to simultaneously image a depth of several millimeters of the vitreous. By adjusting the slit narrower, a finely-focused or thin axial section of the imaged region is selected for imaging.

The light passing slit 22 is redirected by mirror 23 and lens 24 onto a third face 37c of the reflective prism, which rescans the time-varying stationary slit beam across the slit axis, in the same sense as illumination beam 100a is scanned by the opposed prism face 37a, thus sweeping out a real two-dimensional image. This image is received by a camera and viewing system 27. Lens 24 and optics 25 are selected to project the artificial pupil 38 to the correct pupil position, denoted 28, of the camera and viewing system. The optics 25 preferably constitute a zoom system which changes the image magnification of and the exit pupil of the system, but which remains focused on or conjugate to the fixed pupils 38, 14 of the object.

Preferably, various electronic sensors are provided in the system to detect or synchronize the position of the scanned image and features therein. In particular, a CCD detector array 29 is located to receive the slit beam from artificial pupil 38, and angular and distance transducers (not shown) are connected to the scanning prism and each focus adjustment mechanism to provide precise indications of scan direction and focal/zoom parameters.

Several preferred details of construction are particularly worth noting. First, as with the embodiment of FIG. 1, the embodiment of FIG. 3 is adaptable to a binocular viewing system. The stereo base b determined by the two system pupils projected on plane 14 of the eye determines a triangular base, so that precise dimensional measurement of imaged features is effected by analysis of the sensor signals, or of the recorded images.

In the preferred embodiment, the objective assembly preferably includes a pair of back-to-back telecentric lenses which may be moved axially relative to each other to vary the eye focus. The lenses are arranged with the illumination beam's mirror and stop 6 at the front focus of the first lens, and the iris plane 14 at the rear focus of the second lens, such that the light between the two lenses is parallel. Thus, when one of the lenses is moved axially to change the focal region, the entrance and exit apertures in the eye pupil remain in the iris plane at a constant spacing. The first lens or group of lenses scans the slit beam over a wide angular field in the intermediate region, and the second lens or group of lenses includes an aspheric ophthalmic lens to relay the wide angle scan image into the vitreous.

FIG. 4 shows a representation of the objective optics 40, 41, 42 of such a system, corresponding to elements 8, 9a, 12 of FIG. 3. Elements 40, 41 are identical aspheric lenses, and the system is approximately telecentric, requiring minor modification to present a metric, defined by the triangulation base b, which is unchanging with fixed magnification when the lens assembly is moved. A spherical lens 42 relays the intermediate slit image 44 to the vitreous. When using such an objective optical assembly, preferably, a second zoom system is provided at the camera relay optics 25 to vary the magnification of the overall system. Such a second zoom system has constraints on front and rear focus, but unlike the objective system need not preserve angles as is required for scanning the two entrance pupils in the eye iris.

In a prototype embodiment, the slit beam was formed using a thirty micron slit twenty millimeters long, the image of which was expanded to a beam 200 microns wide and 120 millimeters tall, which was relayed by an objective system of lenses having a diameter somewhat over 120 millimeters, using aspheric optics with the sag defined by the conic equation set forth above. The lens diameter was substantially larger than that of the 60 or 90 diopter aspheres commonly used for viewing the interior of the eye, and had a longer focal length to achieve a subject-to-instrument spacing of approximately 50-60 mm. The aspect of the beam tapered, from approximately 200 microns to only 20-30 microns in the focal region in the vitreous. The scanning focus constituted a curved field within the eye in front of the retina, and in one embodiment the scanned image constituted about a sixty degree field in the vitreous, with the focal region adjustable from the retina to approximately six millimeters forward of the retina. The overall range was set by the limits of a mechanical stage holding the objective assembly, and is not believed to be a limitation of the optics; thus the full vitreous could be visualized by extending the mechanical focus adjustment. Further field coverage beyond sixty degrees is obtained by adding a contact lens of high refractive index, formed, e.g., of zinc sulfide (n=2.38).

FIG. 4A illustrates the presently preferred dual telecentric objective assembly for achieving a sixty degree scan. In this embodiment, first and second aspheres 40a, 41a are placed at the mirror and eye stages respectively, and the eye stage further includes a spherical lens 42a which together with the asphere 41a directs the intermediate slit image 44a through the iris into the vitreous. The double lens arrangement near the eye provides a thinner beam with approximately twice the angular scan range of the configuration shown in FIG. 4. An optional high-index contact lens 43a shown in phantom, serving as a minifier, can further increase the scan range by up to a factor of two.

Figure 8:
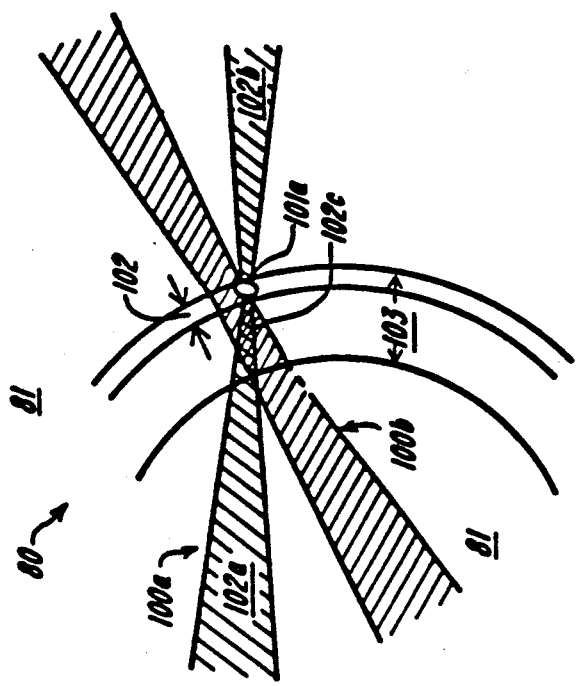
FIG. 8 illustrates optical paths through a region of the vitreous scanned by the invention.

FIG. 8 below shows an enlarged sectional view of the eye region 80 indicated by VIII in FIG. 4, showing the slit illumination and imaging geometry. An anterior region 81 of vitreous humor is crossed by the illumination beam 100a which focuses to a narrow skirt 101a at the focus of the eye optics. The skirt sweeps through a curved "plane" 102 in the vitreous as the mirror 7, 107 or 37a scans, and at each instant a narrow slanted wedge 102a or 102b is also illuminated ahead of and behind the plane 102. The objective assembly and stop 38 collect light passing through the observation window 14b which emanates from an "observation beam" 100b which crosses illumination beam 100a at an angle. Observation beam 100b also tapers to a narrow skirt as it is focused in the same region by the optical assembly. Because of the obliqueness of the illumination and observation paths, the observation beam effectively picks up illumination light only from a portion 102c of the illumination beam adjacent to plane 102, where the two beams intersect. Thus, as the beams are scanned, the collected light is gathered from a somewhat broader region 103, surrounding the plane 102, determined by the intersection of the two beams.

It will be noted that observed region defined by the intersecting loci of the illumination and observation beams is a thin, substantially axially-oriented, wedge 102c. The size of the region of intersection is determined by the size and position of the beam-forming slits. Thus, as the narrow focal skirt of one or both intersecting beams is made wider, by increasing the width of slit 6 or 38, the total thickness of the imaged plane is made thicker. Similarly, by laterally translating a slit, the region of intersection of the beam defined by that slit is moved axially forward or backward along the beam defined by the other slit. The contrast may be varied by either of these adjustments to achieve optimum imaging.

This geometry applies to all embodiments of the apparatus described in this patent application, and while it hs been described for an "illumination" and "observation" beam, where the illumination slit is considered fixed, it also applies, mutatis mutandis, with the beams interchanged. In particular, each beam may be alternately employed for illumination and imaging to achieve a binocular apparatus.

Figure 5:
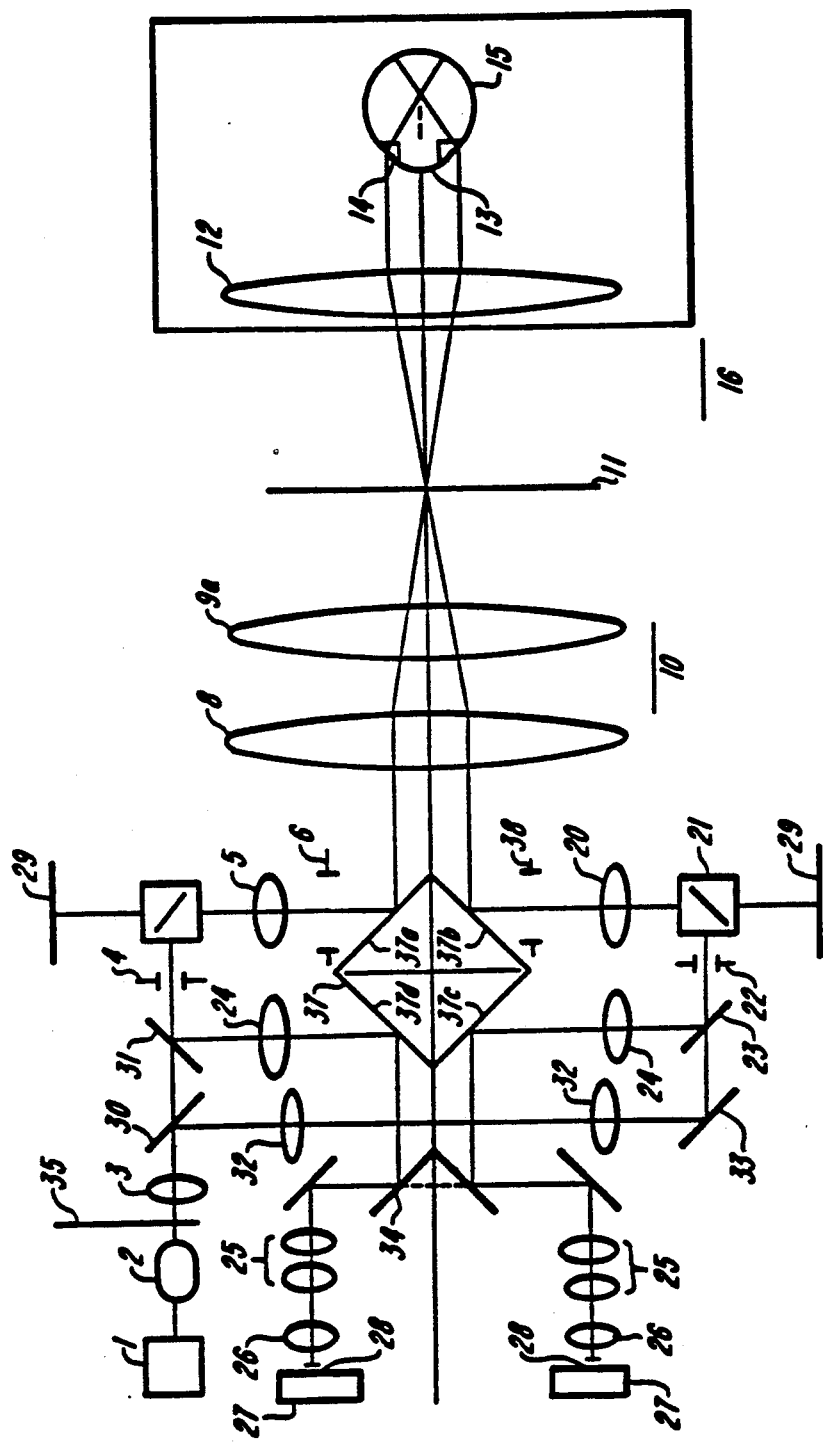
FIG. 5 shows a binocular construction based on the embodiment of FIG. 3.

A modification of the embodiment of FIG. 3 to produce binocular images for metric imaging records is illustrated in FIG. 5. As in the monocular/binocular systems of FIGS. 1 and 2, the front objective optics are identical for both the monocular and binocular systems. In the embodiment of FIG. 5, however, stereo imaging is achieved by the addition of an optomechanical trigger or optical path-switching assembly which alternately passes illuminating or observation light through each pupil aperture at the eye, and by the provision of duplicate descanning, rescanning and camera optics for receiving the observation light from each pupil.

The stereo vitreous camera of FIG. 5 employs the same scanning prism and objective optical assembly as the monocular embodiment of FIG. 3. As in the monocular embodiment, a laser source 1, beam expander 2, and cylindrical condenser lens 3, together with an illumination pupil 35, produce a narrow illumination beam. In this embodiment, however, an optomechanical trigger assembly, illustratively consisting of a plurality of beam splitters, 30, 31, 33, 23, alternately passes the narrow illumination beam, directly or via a pair of symmetrically placed relay lenses 32, to one of two beam-defining slit diaphragms 4, 22 to form an illumination beam that is directed by the scanning and objective optical assembly through windows 14a or 14b, respectively, into the vitreous.

In this embodiment, three of the beamsplitters 30, 31 and 23 are rotation beamsplitters; each has an axis of rotation perpendicular to the face of the beamsplitter, and a reflective region of the face which is decentered in vertical direction as much as the dimensions of the device allow. The phase of rotation of two beamsplitters 30 and 31 is the same, and the phase of a third beamsplitter 23 is displaced by $\pi$. Thus, when the illumination light passes through the beamsplitters 30 and 31, the observation beam is reflected from the beamsplitter 23, toward the camera 27b, and when beamsplitter 30 is in its reflective position, it directs the illumination beam through splitter 23 while the observation beam is reflected by splitter 31 toward the camera 27a. All three beamsplitters are preferably rotated in synchrony using one motor and a common mechanical drive, with conic gears.

More specifically, after the illumination is directed by the beamsplitters of the optomechanical trigger to a beam-forming slit 4 or 22, the beam passes through the illumination lenses, 5 or 20, and comes to the first face 37a or 37b of the scanning prism 37. The beam is reflected from the first face of the scanning prism 37 and passes through optical components 8, 9a, 12 to the pupil 14a or 14b of the eye 15. After reflecting from the vitreous in the object focal plane, the observation beam passes through the same optical components 12, 9a, 8 and comes to the second surface of the scanning prism 7, where it descans and passes through the lens, 20 or 5, which forms a stationary image on the other beam-forming slit diaphragm, 22 or 4, alternately, depending on the position of the beamsplitters. After reflecting from the mirror 23 or 31 and passing through one of the symmetrically placed lenses 24 it comes to a third reflecting face of the scanning prism, either 37c or 37d, where it rescans again and is directed to one side of a stereomicroscope assembly. The stereomicroscope assembly includes a prism device 34 for adjusting the eye base for stereo viewing and also includes optical imaging components 25 and 26 and two cameras 27a, 27b.

Figure 6:
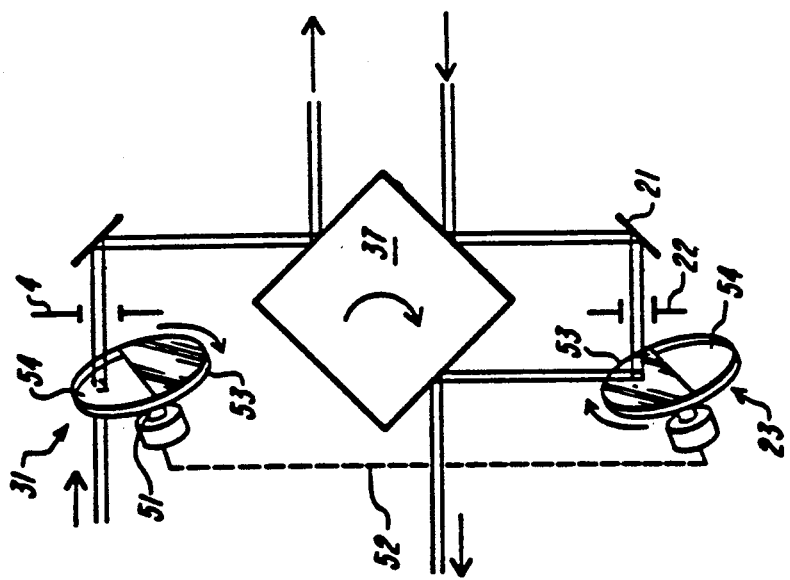
FIGS. 6 and 7 show details of the beam splitting and synchronizing optics for the binocular construction of FIG. 5.

FIG. 6 illustrates the arrangement of the out-of-phase beam splitters 31, 23. Each consists of a rotating disk 50 which turns about an axis or shaft 51 perpendicular to the face of the disk, driven by a common drive gearing 52. Each disk 50 has a reflective portion 53 and a light transmissive portion 54 which in alternate half-cycles are rotated into a position to reflect or transmit the light beam. In the FIGURE, beamsplitters 31, 23 are shown with illumination beam entering via beamsplitter 31, and the observation beam being reflected via beamsplitter 23.

Figure 7:
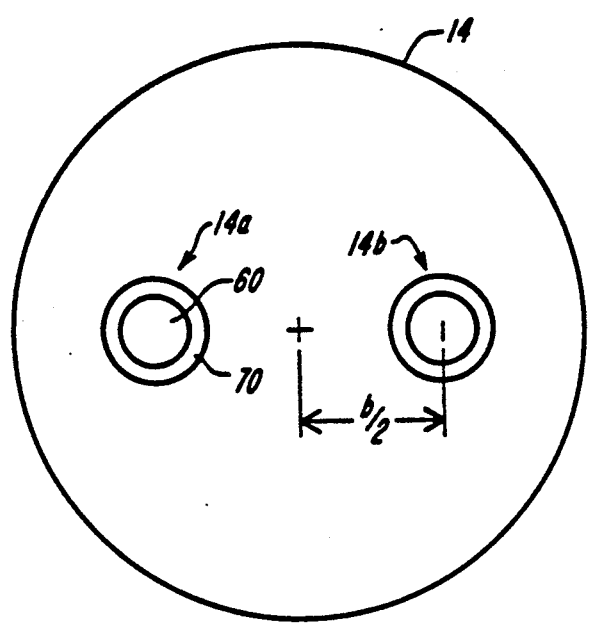

FIG. 7 is a front view of a subject's eye showing the arrangement of pupils 14a, 14b in the iris 14. Each pupil is offset from the center of the iris by a distance b/2, which, as noted above, is preferably maintained fixed to provide a constant metric for observations. Each pupil is schematically shown as having a small central portion 60, representing the aperture used for illumination, and a concentric surrounding portion 70 of greater area, representing the area through which observation light is collected. The dimension of observation aperture 70 is substantially determined by the width of the artificial pupil diaphragm aperture 38 used for collecting observation light and described above in connection with FIG. 3.

This completes a description of a vitreous camera according to the invention, and several illustrative details, variations and embodiments, as well as methods of imaging the vitreous. The invention being thus disclosed, further variations will occur to those skilled in the art, including substitutions for different elements of a disclosed embodiment, as well as adaptations of the invention to related instruments or methods of using such instruments. Thus, it will be understood that the invention is not limited to the precise instrument or arrangements of optical elements described above, but broadly includes further and related structures and methods of use within the scope of the invention, as set forth and defined by the claims appended hereto.

We claim:

1. An instrument for imaging the vitreous humor of the eye, comprising
   a light source,
   means for forming a slit illumination beam,
   a first scanning mirror for scanning the slit illumination beam onto an objective optical system,
   an objective optical system located to project said scanning slit illumination beam through a first region of the pupil plane of the eye to a focal region in the vitreous and to form an observation beam of reflected light reflected at an angle to said slit beam through a different region of the pupil plane of the eye, said objective optical system including an aspheric opthalmic lens for relaying a wide angle scan intermediate illumination image into the vitreous humor, an observation slit conjugate to said focal region, a second scanning mirror for receiving said observation beam from said objective optical system and directing it at the second slit, said second scanning mirror being synchronized with said first scanning mirror so as to descan light reflected from said focal region in the vitreous and maintain the descanned light stationary at said second slit, and means for forming an image from the stationary descanned light at said observation slit.

2. An instrument according to claim 1, wherein said first and second scanning mirrors are a single mirror surface and said objective optical system includes prism means for providing two optical paths through said system on opposed sides of a central axis such that said slit illumination beam and observation beam strike said single mirror surface at a common region but at different angles.

3. An instrument according to claim 1, wherein the means for forming an image from said stationary descanned light includes means for scanning an image of said second slit to sweep out a two dimensional image of the focal region in the vitreous.

4. An instrument according to claim 3, wherein said means for scanning an image of said second slit includes means for reflecting an image of said slit off a mirror surface opposed to and moving synchronously with said first scanning mirror.

5. An instrument according to claim 3, wherein said means for forming an image includes means for forming a pair of stereo images, each image of the pair being formed of light received from one of said first and second regions.

6. An instrument according to claim 3, wherein said means for forming an image includes means for forming a stereo image from descanned light received through said first and second regions.

7. An instrument according to claim 6, further comprising an optomechanical trigger located in the illumination and observation paths for alternately interchanging the direction of illumination and of observation through said first and second regions, such that both regions are used for observation and illumination in alternating trigger cycles.

8. An instrument according to claim 6, wherein the objective optical system includes means for varying the focal region in the vitreous while maintaining a fixed triagulation base between said first and second regions.

9. An instrument according to claim 1, wherein said first and second scanning mirrors are first and second faces of a mirror prism, and wherein said means for forming an image includes means for scanning one or more observation means by reflection from third and fourth faces of the mirror prism.

10. An instrument according to claim 1, further comprising means for varying the width of the second slit to effect a fine resolution of features in the vitreous.

11. An instrument according to claim 1, further comprising means for laterally shifting the position of a said slit to vary the depth of a region of vitreous humor which is observed.

12. An instrument according to claim 1, further comprising a stop conjugate to the pupil plane and mounted to move with a scanning mirror to effect a wide angle scan without occlusion as the mirror turns.

13. An instrument according to claim 1, wherein the objective optical system includes a first telecentric lens assembly for receiving a scanned illumination beam from the first scanning mirror and forming an intermediate scanning image, and a second lens assembly telecentric with the iris of the subject's eye for imaging the intermediate scanning image in the vitreous.

14. An instrument according to claim 1, wherein the objective optical assembly further includes a contact lens of high refractive index.

15. A method of imaging the vitreous humor of an eye, such method comprising the steps of forming a slit illumination beam and scanning the beam with a first scanning element to produce a scanning slit illumination beam, providing an objective optical system for relaying said scanning beam along a first path through a first region of the iris of the eye into a focal region in the vitreous, providing a second scanning element to receive reflected light from the vitreous along a second path through a second region of the iris, said first and second paths both being formed by said objective optical system but said first and second regions being distinct, operating said second scanning element synchronously with said first scanning element to direct the reflected light through an aperture having a conjugate image at said second region, and positioning a second slit conjugate to said focal region to receive the light directed through the aperture thereby producing a time-varying slit image representative of a scan across said focal region.

16. The method of claim 15, wherein said step of providing an objective optical system includes providing a dual telecentric system between said first scanning element and the iris of the eye.

17. The method of claim 15, further comprising the step of providing an optical trigger for alternately directing illumination along the first path while observing along the second path, and directing illumination along the second path while observing along the first path.

18. The method of claim 15, wherein the step of positioning includes selectively varying the lateral position or width of the slit to determine an axial dimension of the imaged focal region.

19. Apparatus for imaging vitreous humor of a subject's eye, such apparatus comprising an objective optical assembly including a first end assembly telecentric with the iris of the eye and a second end assembly telecentric with at least one aperture conjugate to the iris, such that said objective optical assembly determines a pair of fixedly spaced first and second pupil apertures in the iris conjugate to said at least one aperture a scanning mirror element which simultaneously scans an illumination beam through said objective optical assembly and first pupil aperture into the vitreous, and scans a second beam received through said second pupil aperture and optical assembly, said illumination beam and said second beam being directed along distinct optical paths by said scanning mirror element a prism in a path with said scanning mirror element and said objective optical assembly for maintaining said illumination beam and said second beam at different incidence angles to a single face of the scanning mirror element, and a slit aperture said scanning mirror element being positioned to direct said second beam at said slit aperture, and said slit aperture being located conjugate to a region of the vitreous at which said illumination beam is directed by said scanning mirror element said prism and said objective optical assembly, whereby the light flux at said slit aperture is a time-varying line image of the region of the vitreous.

20. Apparatus according to claim 19, further comprising lateral adjustment means for varying at least one of the lateral position and width of the slit aperture.

21. Apparatus according to claim 20, further comprising means for forming a two-dimensional image from said time-varying line image.

22. Apparatus according to claim 20, wherein said scanning mirror element has first and second co-rotating mirror faces which scan said illumination and said second beam, respectively.

23. Apparatus according to claim 19, further comprising means for forming a stereo image of the region of the vitreous from light reflected by said scanning mirror element.

24. An improved method of scanning and imaging a region of the eye through a common objective optical assembly, wherein the improvement comprises the steps of directing an illumination beam at a front surface of a two-sided scanning mirror in the region of a turning axis to scan the illumination beam across the objective optical assembly, and directing an observation beam received through the optical assembly to a rear surface of the two sided scanning mirror in the region of the turning axis, thereby achieving beam separation with little mechanical scan distortion.

25. The improved method of claim 24, wherein the step of directing the observation beam to a rear surface of the scanning mirror comprises the steps of directing the observation beam at said front surface at an angle of incidence different from that of the illumination beam to separate the observation beam from the illumination beam, and directing the separated observation beam to the rear surface.

26. The method of claim 25, wherein the step of directing the observation beam at a different angle of incidence is performed by providing a prism in the objective optical assembly located such that the illumination beam passes through a face of the prism and the observation beam passes through a different face of the prism.

27. The method of claim 26, further comprising the step of providing a stereo imaging apparatus for forming an image from the observation beam after reflection from the rear surface of the scanning mirror.

28. An instrument for imaging the vitreous humor of the eye, comprising a light source, means for forming a slit illumination beam, a single mirror surface for scanning the slit illumination beam onto an objective optical system, an objective optical system including a prism for providing two optical paths through said system on opposed sides of a central axis which strike said single mirror surface at a common region but at different angles, said prism being located to project said scanning slit illumination beam through a first region of the pupil plane of the eye to a focal region in the vitreous and to form an observation beam of reflected light reflected at an angle to said slit beam through a different region of the pupil plane of the eye, an observation slit conjugate to said focal region, said single mirror surface receiving said observation beam from said objective optical system and directing it at the second slit, thereby descanning light reflected from said focal region in the vitreous and maintaining the descanned light stationary at said second alit, and means for forming an image from the stationary descanned light at said observation slit.

29. An instrument according to claim 28, wherein said objective optical system includes a lens and a prism, said prism having dihedral faces oriented to place said single mirror surface in illumination and observation paths through said first and second regions, respectively, of the pupil plane.

30. An opthalmic imaging system comprising a light source means including a first slit for forming a slit illumination beam a scanning element having first, second, third and fourth co-rotating scanning faces an objective optical system located for receiving said slit illumination beam and projecting it to a focal region in tissue of a subject's eye and for receiving light from the focal region and projecting it to the second face of the scanning element a second slit conjugate to said focal region, said second face directing light received from the focal region at said second slit and descanning said light to maintain the descanned light stationary at said second slit as a time-varying line image means for alternately interchanging the direction of illumination and observation paths such that the time varying line image is alternately formed at said first slit and said second slit stereo imaging means for imaging said first and second slits on said third and fourth co-rotating scanning faces, respectively, to sweep out a pair of stereo line scan images from light descanned by said first and second faces.

* * * * *